United States Patent [19]

Moshammer et al.

[11] Patent Number: 5,122,633
[45] Date of Patent: Jun. 16, 1992

[54] METHOD AND APPARATUS FOR RADIATION MICROWAVE ENERGY INTO MATERIAL CONTAINING WATER OR MIXED WITH WATER

[75] Inventors: Wolfgang Moshammer, Schörgelgasse 26,, A-8010 Graz; Erwin Berger, Sonnenrain 18, A-8750 Judenburg; Johann Freissmuth, Raiffeisenstrasse 58a, A-8010 Graz; Helmut Freiberger, Vienna, all of Austria

[73] Assignees: Wolfgang Moshammer, Graz; Erwin Berger, Judenburg; Johann Freissmuth, Graz, all of Austria

[21] Appl. No.: 533,760

[22] Filed: Jun. 6, 1990

[51] Int. Cl.⁵ .............................................. B23K 15/10
[52] U.S. Cl. ....................... 219/10.55 A; 219/10.55 R; 219/10.55 M; 219/10.57; 374/14; 374/17; 34/60
[58] Field of Search .............. 219/10.55 A, 10.55 R, 219/10.57, 10.55 M; 374/14, 17, 60

[56] References Cited

U.S. PATENT DOCUMENTS

| | | | |
|---|---|---|---|
| 4,250,628 | 2/1981 | Smith et al. | 34/1 |
| 4,312,640 | 1/1982 | Verrando | 55/58 |
| 4,313,786 | 2/1982 | Smith | 159/22 |
| 4,423,303 | 12/1983 | Hirose et al. | 219/10.55 A |
| 4,490,287 | 12/1984 | Hardwick et al. | 252/629 |
| 4,606,650 | 8/1986 | Harris | 374/14 |
| 4,622,446 | 11/1986 | Sugisawa et al. | 219/10.55 R |
| 4,637,145 | 1/1987 | Sugisawa | 219/10.55 A |
| 4,715,727 | 12/1987 | Carr | 374/122 |
| 4,882,851 | 11/1989 | Wennersfrum et al. | 34/60 |

FOREIGN PATENT DOCUMENTS

| | | |
|---|---|---|
| 0112295 | 6/1984 | European Pat. Off. . |
| 0287549 | 10/1988 | European Pat. Off. . |
| 3341585 | 5/1985 | Fed. Rep. of Germany . |
| 2612033 | 9/1988 | France . |

*Primary Examiner*—Bruce A. Reynolds
*Assistant Examiner*—Tu Hoang
*Attorney, Agent, or Firm*—Watson, Cole, Grindle and Watson

[57] ABSTRACT

In order to obtain a more homogeneous energy absorption and preset maximum temperatures in an apparatus for radiating microwave energy into water-containing material or material mixed with water, which is introduced into a cavity resonator subjected to microwaves by one or more microwave generators, a pressure and/or temperature sensing device being included, the proposal is put forward that a sealable container be provided for receiving the material to be treated, which should be transparent to microwaves and resistant to gases and pressures, and whose interior should be enclosed by the cavity at a given distance, and that the pressure and/or temperature sensing device be connected with the interior of this container, and further that a device be provided for control of the energy output of the microwave generator, which device should control and maintain constant a preset interior pressure deviating from atmospheric pressure, and which should be connected to the pressure and/or temperature sensing device.

9 Claims, 2 Drawing Sheets

METHOD AND APPARATUS FOR RADIATION MICROWAVE ENERGY INTO MATERIAL CONTAINING WATER OR MIXED WITH WATER

BACKGROUND OF THE INVENTION

This invention relates to a method and apparatus for radiating microwave energy into material containing water or mixed with water, which material is introduced into a resonant cavity subjected to microwaves by one or more microwave generators, a pressure and/or temperature sensing device being provided.

DESCRIPTION OF THE PRIOR ART

A number of applications have become known in which microwaves are used for heating organic matter, in particular, materials containing water. Products range from equipment for cooking or baking to apparatus for sterilizing, disinfecting or dehydrating objects or samples.

In EP-A 0 287 549, for instance, an apparatus is disclosed which is used for heating objects and organisms, in particular for killing or inactivating organisms containing proteins or nucleic acid. In this application the objects or organisms, which are introduced into a cavity resonator, are exposed to microwaves generated by a magnetron. For a homogeneous distribution of energy, and in order to avoid so-called cold spots in the resonant cavity, several magnetrons are provided in a given geometrical pattern, which is designed to make this apparatus particularly suitable for sterilization of medical equipment and for disposal of medical (infectious) waste.

The main disadvantage of this known apparatus is that the temperatures of 100° C. which are obtained in organic matter or moistened materials, are not high enough to destroy spores, for instance, which would require temperatures of 121° C. and more.

Another drawback is that substrates can be heated by direct microwave excitation to a point at which the ignition temperature of paper or textile components is reached or even exceeded.

These problems cannot be solved even by the use of water bags inside the cavity. They have not succeeded in providing the homogeneous distribution of water vapor necessary for adequately moistening the inserted samples or cooling substrates that are directly excited by microwaves.

Besides, it has not been possible with the above apparatus or other known microwave equipment for warming or heating organic matter to prevent the materials to be introduced into the cavity from drying out, which is a disadvantage especially when the preparation or heating of food is concerned.

Another apparatus used for sterilization and disinfection is the autoclave. Its underlying principle is a pressure vessel, possibly evacuated before use, which is filled with water vapor of a predefined temperature. This water vapor has a given thermal energy which is transferred to the material entered into the container. The temperature difference between water vapor and material will result in a heat transfer depending on the thermal conductivity of the material. As a result of this heat transfer the water vapor introduced into the container will cool off, and the pressure container must be newly evacuated and filled with hot steam in order to obtain a given temperature. To obtain a given temperature as quickly as possible, the water vapor must be filled into the pressure vessel at a temperature much higher than the desired temperature of the material, involving the use of additional energy. Besides, the water vapor must heat the walls of the pressure vessel as well, wasting even more energy without contributing to the heating of the material itself. If the material used has poor heat conducting properties and a large volume accompanied by a small surface, it will take a very long time unitl the heat has been transferred from the water vapor to the core of the material, while it is not possible to rule out the surviving of some germs in enclosed spaces, e.g. in plastic tube. Another drawback are the long cycle times of 50 minutes and more. The total amount of energy required will be a multiple of the energy actually going into the material to be heated.

An apparatus of the type mentioned at the beginning of this paper is described in DE-A1 33 41 585, for example. The object to be heated is placed into a pressure-tight chamber with walls of a metallic material, i.e. the actual cavity resonator, the object itself being vacuum-sealed in plastic. As the sealing material is not resistant to the desired pressures of several bar, it will touch parts of the resonator wall.

As is known, however, the resonator wall is the boundary surface at which the electric field strength of the microwave must equal zero; thus the inserted material or the prevailing water vapor will not be heated in the immediate vicinity of the interior surface of the cavity. On the contrary, the water vapor will cool off due to the cooling effect prevailing at the surface of the cavity. The vapor will condense at the cavity surface and collect at the bottom. Therefore the resulting liquid is not subject to the conditions of sterilization and must be considered infectious even after the sterilization process.

Since infectious waste, for example, is entered into the microwave disinfector almost exclusively in special bags designed for this purpose, and as the waste is to be considered non- mixing, the problem mentioned in the above paragraph would arise also with the waste itself, i.e., parts of the waste lying next to the interior surface of the resonator cavity would remain infectious.

SUMMARY OF THE INVENTION

It is an object of this invention to propose a method and an apparatus for radiating microwave energy into material containing water or mixed with water, which should permit a most homogeneous warming or heating of this material, even if the material itself is quite inhomogeneous, the temperature to be obtained in the material being definable over a wide range. In a variant of the invention temperatures at or above the thermal death point of spores should be reached.

In the invention this object is achieved by providing a sealable container transparent to microwaves, which should be gas-tight and pressure-resistant and is designed to receive the material to be treated, whose interior is enclosed by the resonant cavity at a certain distance, and by further providing that the pressure and/or temperature sensing device be connected with the interior of this container, and further that a device be added for control of the energy output of the microwave generator, which device should control and maintain constant a preset interior pressure deviating from atmospheric pressure, and which should be connected to the pressure and/or temperature sensing device. The devices for controlling and maintaining constant a preset interior pressure, which may be above or below atmospheric pressure, will permit varying the temperature prevailing inside the gas- and pressure-tight, sealable container in a wide range, depending on the specific purpose for which it is used. In the interior of the sealed container a relatively high content of water vapor will develop quickly, which will provide the uniform temperature distribution desired and a homogenous heating of the material introduced. Pressure readings are taken either directly via a suitable sensor, or indirectly via the temperature in the gas chamber inside the container. The walls of the gas-tight container will ensure thermal insulation of the interior against the resonant cavity in addition to providing the necessary minimum distance from the cavity wall, which should amount to a quarter of the wavelength used (i.e., 3 cm for 2450 MHZ).

For instruments and equipment operating at pressures higher than atmospheric pressure, in which the material to be treated is sealed in a gas- and pressure-tight vessel and is heated to temperatures above 100° C. by means of microwave energy, the interior pressure increasing due to evaporating material components, it is provided by the invention that the interior pressure of the evaporated matter be measured and microwave irradiation be reduced or stopped as soon as a preset value above atmospheric pressure has been reached, and further that the achieved temperatures and pressures be maintained for a given period in order to establish a uniform temperature distribution between the individual material components, and that pressure be relieved subsequently.

In appliances operating in a pressure range above atmospheric pressure, such as microwave ovens or sterilizers, best operating results and energy savings are achieved by providing them with electronic control circuitry connected to their pressure and temperature sensing devices, in order to control the energy output of the microwave generator required for obtaining and maintaining constant a preset interior pressure at a level above atmospheric pressure.

It is proposed in a variant of the invention that in the instance of material whose water content is too low, water or steam be directly added to this material, i.e., by providing a feed line for water or steam which should be furnished with a valve and connected to the interior of the container.

It is of advantage, in particular for sterilizers, if, according to another proposal of the invention, the material is subjected to an absolute pressure of a level below atmospheric pressure, i.e., some 100 mbar preferably, before microwave energy is coupled in, a vacuum unit being provided for evacuation of the interior, which should be locked by a valve and should be placed outside of the resonant cavity. This will further increase the content of water vapor in the reaction chamber, thus speeding up the processes of heating and temperature equilibration between inhomogeneous material components in the sealed inner container.

For instruments and equipment operating in a partial vacuum it is provided by the invention that the material be subjected to a preset pressure of a level below atmospheric pressure, and that microwave energy be coupled into the material such that it is heated to a temperature below 100° C. and the water contained in it evaporates, and further that the preset pressure be measured and maintained for a given time, and that pressure be relieved afterwards.

This method is particularly well suited for the gentle drying or dehydrating of food (mushrooms, herbs, etc.), the reduced pressure ensuring mild evaporation temperatures for the water contained in these foodstuffs.

An application variant concerning the drying of foodstuffs provides that the vacuum unit include a vacuum pump controlled via the pressure sensing device, which is intended to maintain constant a preset interior pressure below atmospheric pressure.

In the invention the sealable, gas-tight container may be configured as a pressure vessel both for equipment operating above and below atmospheric pressure. The main feature required in this respect is that the pressure vessel must be transparent to the microwave radiation used and resistant to the pressure forces arising.

For microwave ovens and sterilizers the invention finally provides that the sealable, gas-tight container be supported in the cavity and preferably be made of polytetrafluoroethylene. The only requirements the container has to meet in this instance are that it perform a sealing function, have low high frequency losses and high temperature stability. The deformation forces generated in such applications are largely counteracted by the cavity. The distance between charge and cavity wall required in sterilizers is provided here by a suitable wall thickness of the container, which may be made of silicone material.

BRIEF DESCRIPTION OF THE DRAWINGS

The invention will be further described with reference to the accompanying drawings, in which FIG. 1 gives a schematical view of an apparatus of the invention, and FIG. 2 a variant of FIG. 1.

DETAILED DESCRIPTION OF THE PREFERRED EMBODIMENTS

Figure 1:
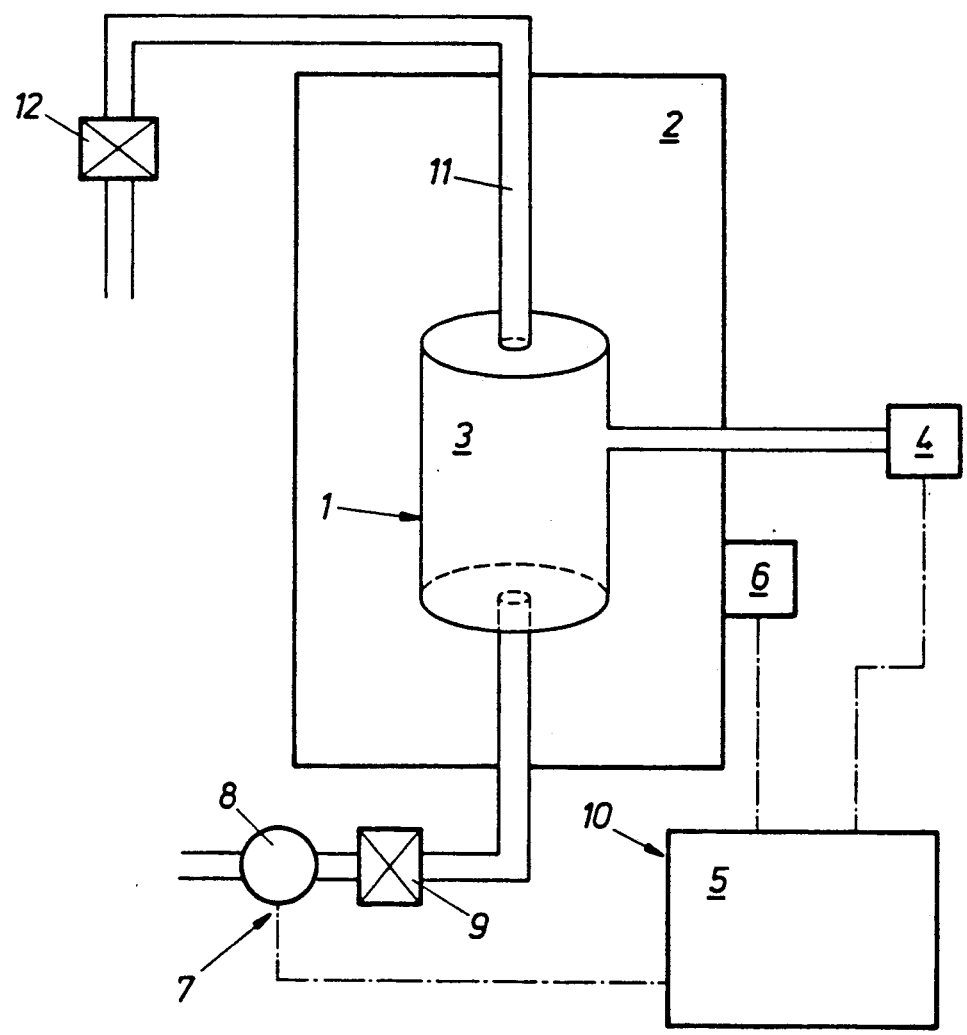

The apparatus shown in FIG. 1 is provided with a gas-tight and pressure-resistant, sealable container 1 receiving the material to be processed, which is enclosed by the resonant cavity 2 at a given distance. The minimum distance between the container interior 3 and the cavity wall is in the range of 3 cm for microwaves of 2450 MHZ. The interior 3 is connected with a pressure sensing device 4 controlling the energy output of a microwave generator 6 by means of an electronic control circuit 5. It would also be possible to measure the interior pressure via a temperature measuring device. The container 1 is further connected with a vacuum unit 7 for evacuation of the container interior 3. The vacuum unit 7 is provided with a vacuum pump 8 controlled by the pressure sensing device 4 via the electronic control circuit 5, and with a valve 9 maintaining the pressure inside the container 1. The electronic control circuit 5 connected with the pressure sensing device 4, and the vacuum unit 7 together with the corresponding control lines form the unit 10 controlling and maintaining constant an interior pressure deviating from atmospheric pressure. A feed line 11 with a metering valve 12 is provided for the addition of water or steam in order to moisten material that is too dry for processing.

If the apparatus of FIG. 1 is operated at more than atmospheric pressure, for instance, as a microwave oven or sterilizer, the following steps should be performed.

The material to be irradiated is introduced into the container 1, e.g., a pressure vessel, through a suitable opening (not shown here). By means of a metering valve 12 water is entered into the pressure vessel 1, either manually or automatically; this step may be omitted if the material itself contains water. The container 1 is then sealed so as to be gas-tight and pressure-resistant. For special applications, for example, for disinfection purposes, the pressure vessel may be evacuated to a pressure of some 100 mbar before applying the microwave energy, such that saturated steam is produced during the subsequent heating process. At the end of the evacuating process the pressure system is left alone and the vacuum unit 7 is switched off. By means of a gyratron, magnetron or klystron tube, or other microwave generators 6 microwave energy is entered into the cavity 2, which will heat the material entered for processing—as far as it lends itself to direct heating by microwave energy—and the water added thereto. The evaporating water will increase the pressure prevailing in the interior 3 of the container 1, and the boiling temperature of the water will rise to more than 100° C. Via the pressure sensing device 4 the microwave generator 6 is controlled by throttling or intermittent switch-off such that a preset pressure value (e.g., 3 bar absolute pressure for sterilizing, and 2 bar absolute pressure for disinfecting) will not be exceeded. The steam produced during this process will fill the entire pressure system, thus representing a homogeneous temperature field; besides, it is maintained at a constant temperature level by the microwave field. The transformation of energy takes place in the water vapor itself. If parts of the inserted material are not heated by microwave energy, heat is transferred from the water vapor to these parts. As a consequence, the entire material is gradually heated to the temperature of the water vapor. If parts of the inserted material are heated by the microwave energy to a temperature higher than that of the surrounding water, heat is transferred from the material to the water or water vapor. As a consequence, these material components (substrates, surgical tools, test tubes) are cooled from the surface, such that they cannot be heated beyond a certain level, in spite of the energy feed. After a predefined operating period it will be noticed that both the inserted material and the water vapor have roughly the same temperature on account of the heat exchange, which means that the temperature of the inserted material can be inferred from measuring the pressure or the temperature of the water vapor. During the entire operating cycle the input of microwave energy is reduced or cut off temporarily in such a way as to ensure that the pressure will not exceed a predefined maximum nor drop below a given minimum, the entire material being subject to a preset temperature for a preset period of time. The input of microwave energy is stopped after a ceratain operating period, and the pressure in the container 1 is relieved and the material removed.

In medium-size and large-size variants, for example, in waste disinfection, the pressure vessel 1 may be made of a material permitting thermal insulation from the resonant cavity 2. This has the considerable advantage that the cavity need not be heated during the heating process of the material, which will lead to extensive savings of energy and time.

The apparatus shown in FIG. 1 may also be used for dehydration of material, such as the gentle drying of herbs, mushrooms, fruit and vegetables. It is also possible, however, to use it in processes of bonding and cementing in order to reduce curing or setting times by desiccation.

The water-containing material is inserted into the container configured as a pressure vessel, which is then sealed so as to be gas-tight. Before microwave energy is applied to the cavity 2 the pressure vessel is evacuated to a preset degree until a given interior pressure will prevail in the cavity interior 3. The water contained in the material is heated to boiling temperature, which may be considerably lower than 100° C. due to the partial vacuum in the container. The partial vacuum is maintained constant by means of the vacuum unit 7 controlled by the pressure sensing device 4. After a preset duration of exposure the hydrated material will be ready. In addition to the energy savings due to the very moderate temperatures required for heating the material in the container, the method proposed by the invention is extremely gentle because of the low evaporation involved, which will leave intact temperature-sensitive substances. This is of importance in the processing of foodstuffs, for example.

Figure 2:
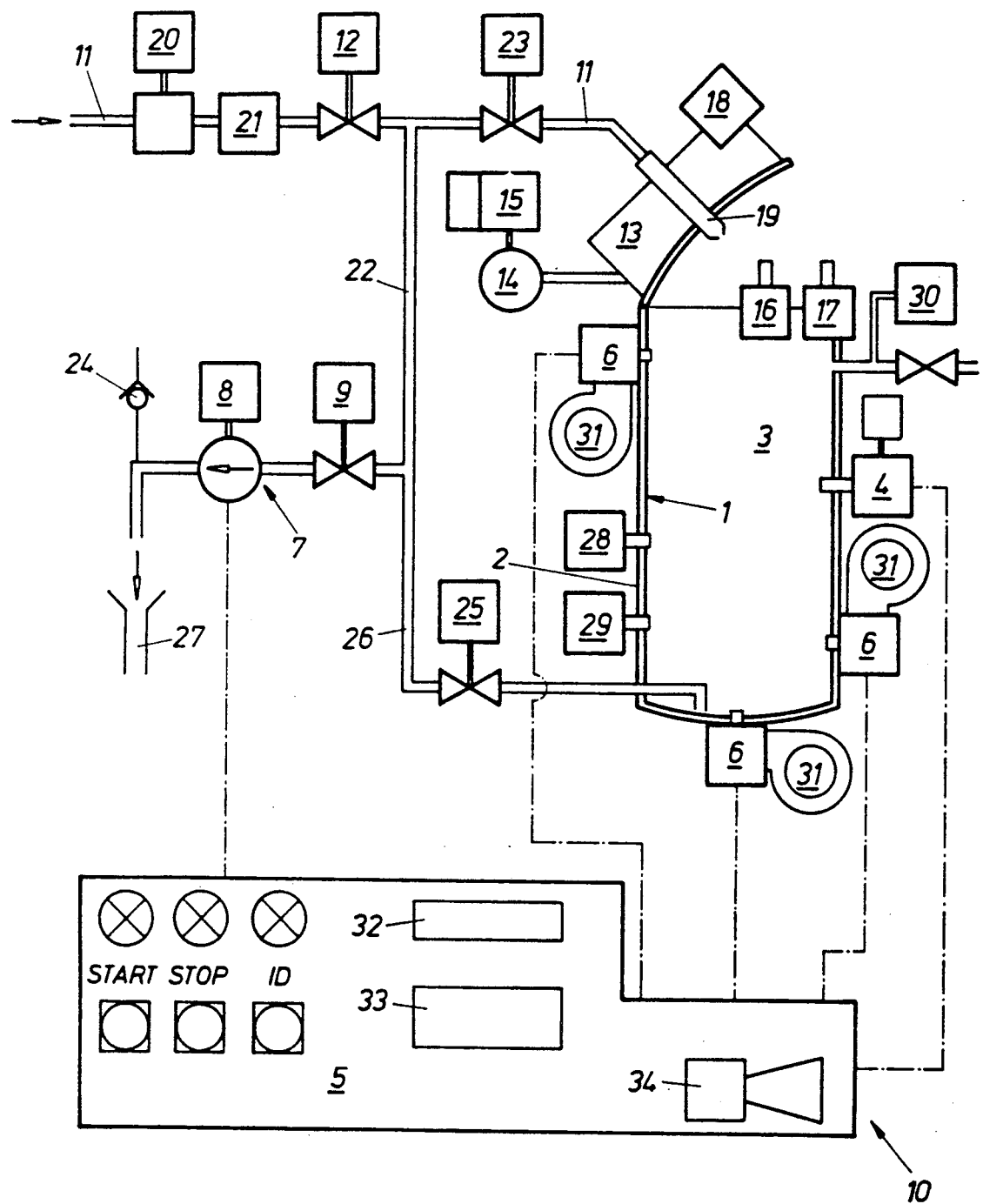

The variant of the invention shown in FIG. 2 is an apparatus used for sterilizing and decontaminating material preferably for disinfection of infectious medical waste.

The resonant cavity 2 is provided with a lining serving as the container 1, whose wall thickness provides the necessary distance from the cavity surface. A lid 13 of the container 1 is shown in its open position. The pressure vessel 1 must be secured against opening during the decontamination cycle. For this purpose the lid 13 is locked automatically at the beginning of the decontamination cycle, i.e., with the use of a locking mechanism 14. The locking mechanism is checked by the corresponding locking contact 15. For safety reasons two stop switches 16, 17 are added to ensure proper closing of the lid 13, one of which is connected to the electronic control circuit 5, and the other one 17 is incorporated into a separate control circuit (not shown here) independent of the rest. The lid 13 has a stray radiation monitor 18 monitoring the maximum power density of leakage radiation permitted by law (5m/Vcm2). For long-term control it is recommended to perform continuous readings of stray radiation during operation and to compare them with a given threshold value. If this limit is exceeded the electronic system will give warning and switch off the apparatus.

In order to fill the entire interior 3 of the pressure vessel 1 with steam at a rated pressure, the necessary amount of water—preferably decalcified—is entered via a spray nozzle 19 atomizing the water from the feed line 11 into small droplets in order to enhance the energy transformation of the irradiated microwaves in the water. In addition to the metering valve 12, the feed line 11 contains a pressure monitoring element 20 as well as a pressure reduction valve 21 ensuring a constant operating pressure.

Before application of the microwaves the vacuum pump 8 generates an abolute pressure of approx. 100 mbar in the container 1. As a consequence an air/steam mixture with a very high percentage of water vapor is produced in the subsequent pressure phase. Due to the high specific heat of the water a considerable amount of heat energy is externally applied to the material to be disinfected, via the water vapor, and even small hollows are supplied with heat energy most satisfactorily. Once the desired partial vacuum has been obtained it it is maintained by the valve 9 even after the vacuum pump 8 has been switched off. In the excess pressure phase the vacuum pump 8 must be protected from the pressure in the interior 3 of the container 1. Evacuation of the container 1 at the beginning of the decontamination process is implemented via the connecting line 22 and the spray nozzle 19 of the injection device, in order to minimize the danger of spreading germs. The pressure-keeping valve 23 in line 11 is kept open until the injection phase has been completed. During the pressure phase in the container 1 the pressure-keeping valve 23 will seal the container 1 against its environment. For ventilation of the container 1 after the final evacuation cycle outside air is admitted into the container 1 via the vacuum valve 24. When the disinfection cycle has been completed and pressure relief has taken place in the container 1, condensed water will form in the interior 3. After the waste water valve 25 has opened, this water, which too is germ-free, is removed from the container 1 via the pump line 26 by means of the vacuum pump 8. The air pumped out during the evacuation process and the condensed water both are drained through the outlet pipe 27.

Since errors of the pressure sensor 4 cannot be ruled out, which may deliver faulty data to the electronic control circuit 5 due to malfunction, independent pressure readings are provided by the manometric switches 28 and 29, which will only give off a digital signal. The switching pressure of switch 28 is below nominal pressure, i.e., at nominal pressure the switch 28 is switched on. If the switch 28 does not respond at nominal pressure, this will indicate a difference in the pressures measured by the pressure sensing device 4 and the manometric switches, and the disinfection process is stopped by the electronic control circuit. The switching pressure of switch 29 is above nominal pressure, i.e., at nominal pressure the switch 29 is switched off. If switch 29 responds at nominal pressure, the disinfection process is stopped again. In order to avoid undesirable pressure rises in the container 1 in case of a failure of the electronic system, a mechanical pressure relief valve 30 is provided.

Connecting lines of the individual electromagnetic or electromechanical valves, or of the stop switches 16, 17 and the manometric switches 28, 29 are not shown in this drawing.

To protect the microwave generators 6 from overheating, they are provided with cooling fans 31.

The electronic control circuit 5 has a panel with a start and a stop key and an ID key for identification or error states in a faulty decontamination cycle.

An alphanumeric display 32 gives both user-relevant operational information and internal operational parameters for the service personnel. For documentation purposes a printer 33 is added, which will print out the main operational parameters (date, time, vacuum, nominal pressure, disinfection time). Faulty operational states may be indicated separately by an acoustic signalling device 34.

The unit referred to as electronic control circuit 5 comprises a control and monitoring unit based on a microprocessor, a power supply and the power electronics, as well as the electronics required for the safe functioning of the apparatus.

We claim:

1. An apparatus for radiating microwave energy into material containing water or into material mixed with water for sterilization of said material comprising:

a resonant cavity subjected to microwaves by at least one microwave generator having a controllable energy output, a sealable container which is transparent to microwaves, is gas-tight and is pressure-resistant, and which is designed to receive said material to be sterilized, said container having walls which are enclosed by and supported from said resonant cavity, a pressure sensing device connected with an interior of said sealable container, a feed line for supplying said sealable container with at least one material of a group consisting of water and steam, and having a valve, and a control unit having a control circuit for controlling said energy output of said microwave generator required for obtaining and keeping constant a present interior pressure higher than standard pressure.

2. An apparatus according to claim 1, further comprising a vacuum unit for evacuation of said interior of said sealable container, said vacuum unit being locked by a valve and placed outside of said resonant cavity.

3. An apparatus according to claim 1, wherein said container is a lining made of polytetra-fluoroethylene.

4. An apparatus according to claim 15, further comprising a temperature sensing device connected with said interior of said sealable container.

5. An apparatus according to claim 1, wherein a thickness of said walls of said sealable container provides a minimum distance from said resonant cavity, which is about 3 cm for a microwave frequency of 2450 MHZ.

6. An apparatus according to claim 1, wherein said resonant cavity and said sealable container are locked by a common lid having a locking mechanism.

7. A method for radiating microwave energy into material containing water or into material mixed with water to sterilize said material, which method comprises the steps of:

a) sealing said material in an interior of a gas-tight and pressure-resistant container, which is transparent to microwaves, b) heating said material to temperatures above 100° C. and increasing an interior pressure by means of microwave energy, c) measuring the interior pressure in said gas-tight and pressure-resisitant container, d) reducing microwave irradiation when said measured interior pressure reaches a preset pressure value, and e) maintaining said temperature above 100° C. and said interior pressure for a given period to establish a uniform temperature distribution inside said gas-tight and pressure-resistant container.

8. A method according to claim 7, before heating said material to a temperature above 100° C. and increasing the interior pressure, at least one material of a group consisting of water and steam is directly added to material whose water content is low.

9. A method according to claim 7, wherein said gas-tight and pressure-resistant container is evacuated before heating said material to a temperature above 100° C. and increasing the interior pressure.

* * * * *